United States Patent [19]

Otake et al.

[11] Patent Number: 4,587,237

[45] Date of Patent: May 6, 1986

[54] MYCOTRIENIN-RELATED COMPOUNDS

[75] Inventors: Noboru Otake, Yokohama; Haruo Seto, Hachioji; Tetsuo Sasaki, Kounosu; Masanori Sugita, Sakado; Shigeru Hiramoto, Kawagoe, all of Japan

[73] Assignee: Nisshin Flour Milling Co., Ltd., Japan

[21] Appl. No.: 773,445

[22] Filed: Sep. 6, 1985

[51] Int. Cl.[4] ............... A61K 31/395; C07D 225/06; C12P 17/10
[52] U.S. Cl. ............................. 514/183; 260/239.3 B
[58] Field of Search ................ 260/239.3 B; 514/183

[56] References Cited

U.S. PATENT DOCUMENTS

| | | | |
|---|---|---|---|
| 4,261,986 | 4/1981 | Sasaki et al. | 260/239.3 B |
| 4,421,687 | 12/1983 | Hasegawa et al. | 260/239.3 B |
| 4,421,688 | 12/1983 | Muroi et al. | 260/239.3 B |
| 4,521,339 | 6/1985 | Otake et al. | 260/239.3 B |

*Primary Examiner*—Robert T. Bond
*Attorney, Agent, or Firm*—Abelman, Frayne, Rezac & Schwab

[57] ABSTRACT

Mycotrienin-related compounds called the T-23-VIII and T-23-IX substances. These substances are isolated and characterized by structural formula and other identifying data. These substances are useful in the treatment of tumors.

2 Claims, 3 Drawing Figures

MYCOTRIENIN-RELATED COMPOUNDS

FIELD OF THE INVENTION

This invention relates to mycotrienin-related compounds having new chemical structures. More particularly, the invention relates to new compounds called T-23-VIII and T-23-IX which are expected for use in medicines because of their having anti-tumor activities.

BACKGROUND OF THE INVENTION

We were successful in ascertaining the presence of T-23-I and T-23-II with ansamycin skeleton having anti-tumor activities in the fermentation product of a new strain *Streptomyces rishiensis* T-23 (deposited at "Fermentation Research Institute, Agency of Industrial Science & Technology, MITI(Japan)" under the deposit No. FERM P-6141), and previously proposed the processes for the production of T-23-I and T-23-II as disclosed in Japanese Patent Application Nos. 189237/1981 and 189238/1981 (laid open to public as L-O-P Publication Nos. 94393/1983 and 92662/1983, respectively). A U.S. patent application based on these Japanese patent applications was issued as U.S. Pat. No. 4,521,339 on June 4, 1985. According to the abovementioned processes, the T-23 strain was cultured according to the conventional method for the culture of Actinomyces strain. The culture broth obtained was divided into mycelia and a supernatant. An active fraction was extracted with acetone-water from the mycelia. The extract containing the active fraction was filtered. The filtrate was passed through a nonionic exchange resin to effect absorption of the active fraction thereon, followed by elution with a solvent such as acetone or a lower alcohol. The active fraction was also extracted with an organic solvent directly from the supernatant. The two extracts obtained were combined, and the organic solvent was removed from the mixture to give an aqueous phase which was extracted with a water-immiscible solvent such as chloroform or ethyl acetate and concentrated. Thereafter, the concentrate was charged with an aliphatic hydrocarbon solvent to precipitate the active fraction. The active fraction was adsorbed onto a silica gel column. After washing with benzene, the column was eluted with benzene-acetone (4:1) to obtain a T-23-I containing solution and with benzene-acetone (7:3) to obtain a T-23-II containing solution.

SUMMARY OF THE INVENTION

As a result of further study, we have found that after obtaining the T-23-I containing solution by elution of the above-mentioned silica gel column with benzene-acetone (4:1), the elution is further continued with the same solvent, whereupon a slight amount of other active substance is eluted therefrom, and that after obtaining the T-23-II containing solution by elution of said silica gel column with benzene-acetone (7:3), the elution is further continued with the same solvent, whereupon a slight amount of different active substance is eluted therefrom. We have accomplished the present invention after isolation of slight amounts of these active substances and confirming physical properties thereof.

DETAILED DESCRIPTION OF THE INVENTION

Figure 1:
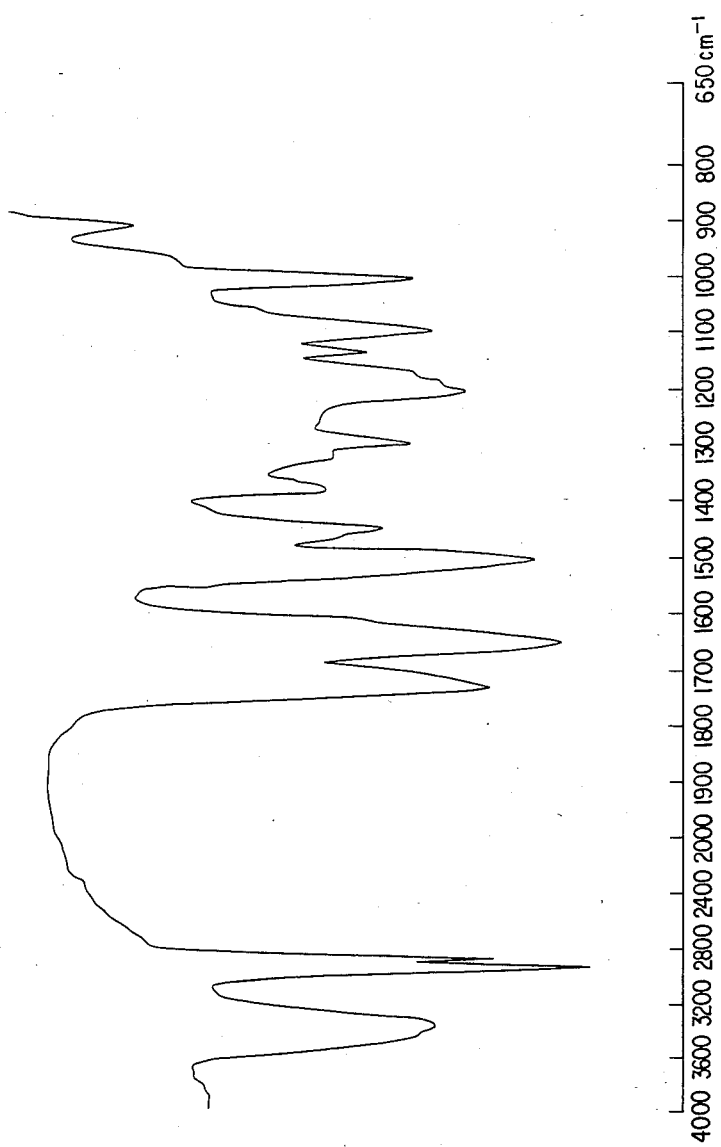
FIG. 1 is infrared absorption spectrum of T-23-VIII.

According to the invention, the aforesaid silica gel column was eluted with benzene-acetone (4:1), and the eluate was fractionated in separate portions. Each of the fractions was subjected to silica gel thin layer chromatography and developed twice with ethyl acetate/benzene (1:1), whereupon a trace amount of substance ($R_f = 0.56$) different from T-23-I ($R_f = 0.58$) was confirmed to be present in the fraction obtained after elution of the fraction containing T-23-I. We named this substance T-23-VIII.

Furthermore, in the case where the aforesaid silica gel column was further eluted with benzene-acetone (7:3), similarly the eluate was fractionated in separate portions, and each of the fractions was subjected to silica gel thin layer chromatography and developed with a solvent system of benzene/chloroform/methanol (3:7:3), whereupon a trace amount of substance ($R_f = 0.55$) different from T-23-II ($R_f = 0.56$) was confirmed to be present in the fraction obtained after elution of the fraction containing T-23-II. We named this substance T-23-IX.

The T-23-VIII and T-23-IX substances stand in the same reversible oxidation-reduction relationship to the T-23-I and T-23-II substances. That is, the T-23-VIII substance was readily reduced to the T-23-IX substance when a solution of the T-23-VIII substance in methanol was charged with a small amount of hydrosulfite and stirred. Similarly, the T-23-IX substance was readily oxidized to the T-23-VIII substance when a solution of the T-23-IX substance in methanol was charged with a small amount of ferric chloride and stirred.

The physicochemical properties of the T-23-VIII and -IX substances are shown below.

T-23-VIII substance

1. Appearance: Yellow amorphous powder
2. Structural formula:

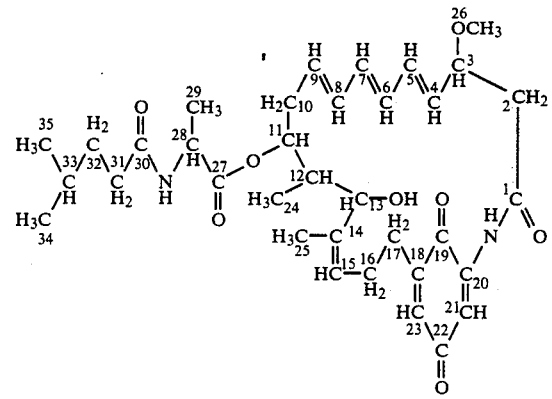

3. Molecular weight: M+624
4. Elementary analysis: Calc. for $C_{35}H_{48}N_2O_8$: 67.31% C, 7.69% H; 4.49% N; 20.51% O. Found: 66.82% C; 8.07% H; 4.51% N; 20.60% O.
5. $[\alpha]_D^{25} = +69.4°$ C. (C=0.144, $CH_3OH$)
6. m.p.: 109° C.
7. UV absorption spectrum (in methanol) λmax 262 nm (ε26,700)
271 nm (ε38,600)
281 nm (ε28,000)
381 nm (ε2,200)

8. IR absorption spectrum (in KBr) (see FIG. 1)

| λ max | 3400 | 2930 | 1730 | 1650 |
|---|---|---|---|---|
| | 1500 | 1450 | 1370 | 1290 |
| | 1200 | 1130 | 1000 | 900 cm$^{-1}$ |

9. Solubility:

Soluble in methanol, ethanol, acetone, ethyl acetate, chloroform and pyridine, Insoluble in n-hexane, petroleum ether and water 10. $^{13}$C-NMR spectrum chemical shift (in CD$_3$OH)

| No. | δ c * |
|---|---|
| 1 | 169.4 (s) |
| 2 | 45.2 (t) |
| 3 | 79.2 (d) |
| 4 | 131.5 (d) |
| 5 | 133.9 (d) |
| 6 | 129.6 (d) |
| 7 | 133.9 (d) |
| 8 | 133.3 (d) |
| 9 | 129.6 (d) |
| 10 | 33.4 (t) |
| 11 | 75.4 (d) |
| 12 | 40.0 (d) |
| 13 | 68.1 (d) |
| 14 | 140.0 (s) |
| 15 | 122.4 (d) |
| 16 | 25.8 (t) |
| 17 | 29.6 (t) |
| 18 | 137.8 (s) |
| 19 | 188.4 (s) |
| 20 | 145.4 (s) |
| 21 | 114.6 (d) |
| 22 | 182.5 (s) |
| 23 | 133.3 (d) |
| 24 | 9.9 (q) |
| 25 | 21.0 (q) |
| 26 | 57.0 (q) |
| 27 | 173.0 (s) |
| 28 | 48.9 (d) |
| 29 | 17.7 (q) |
| 30 | 174.0 (s) |
| 31 | 34.9 (t) |
| 32 | 34.9 (t) |
| 33 | 28.0 (d) |
| 34 | 22.5 (q) |
| 35 | 22.5 (q) |

* Multiplicity in off-resonance spectrum

Figure 2:
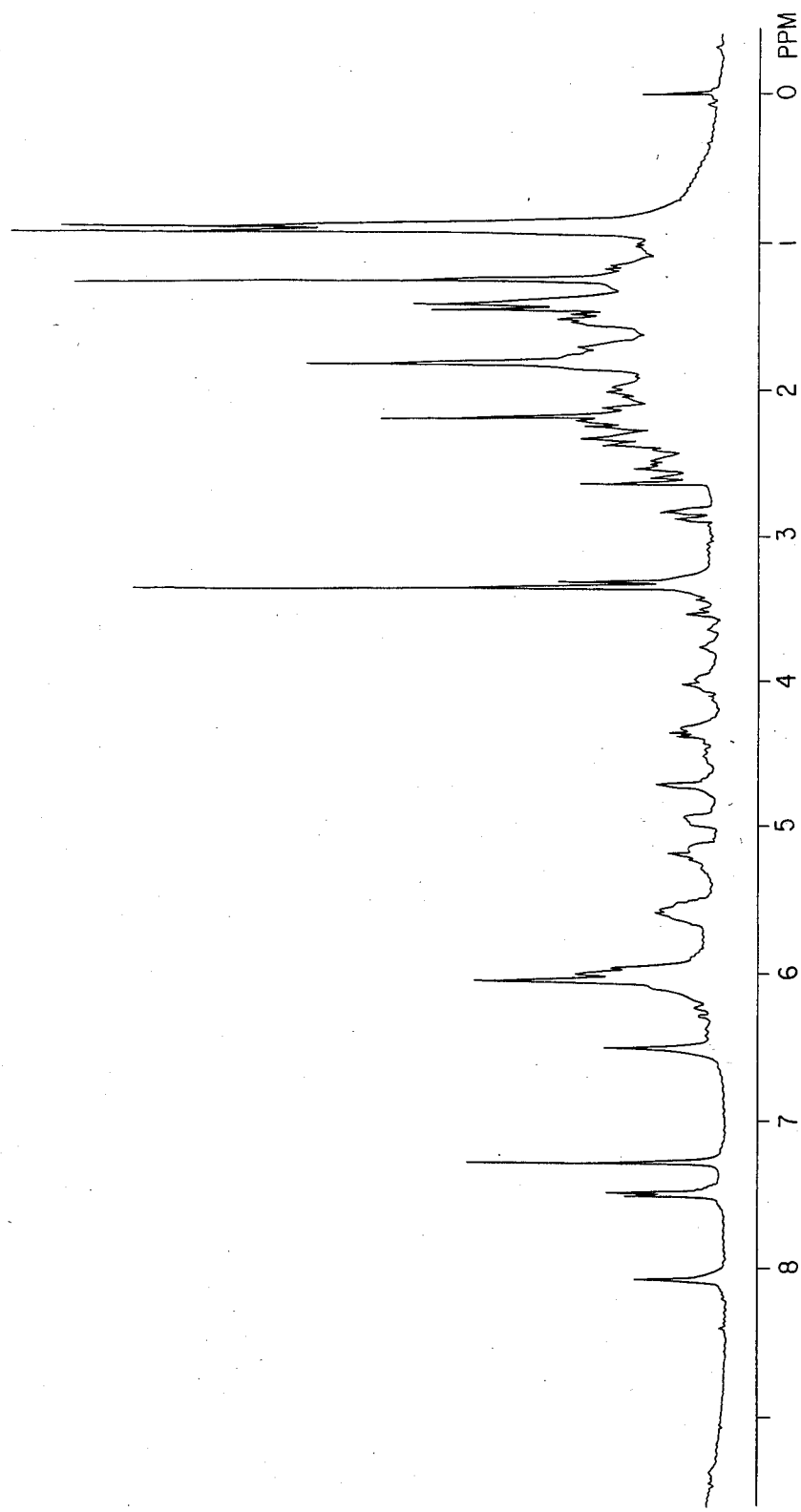
FIG. 2 is NMR spectrum of T-23-VIII.

11. $^1$H-NMR spectrum (in CDCl$_3$) (see FIG. 2)

T-23-IX substance

1. Appearance: colorless amorphous powder
2. Structural formula:

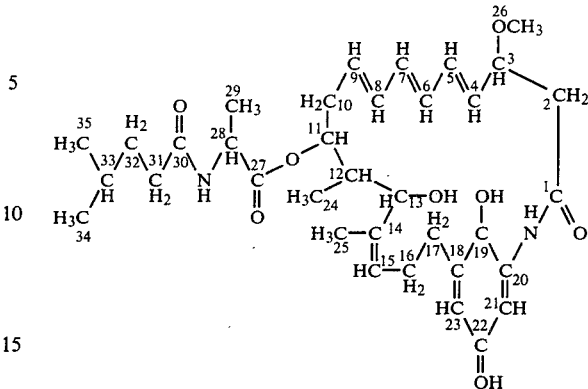

Figure 3:
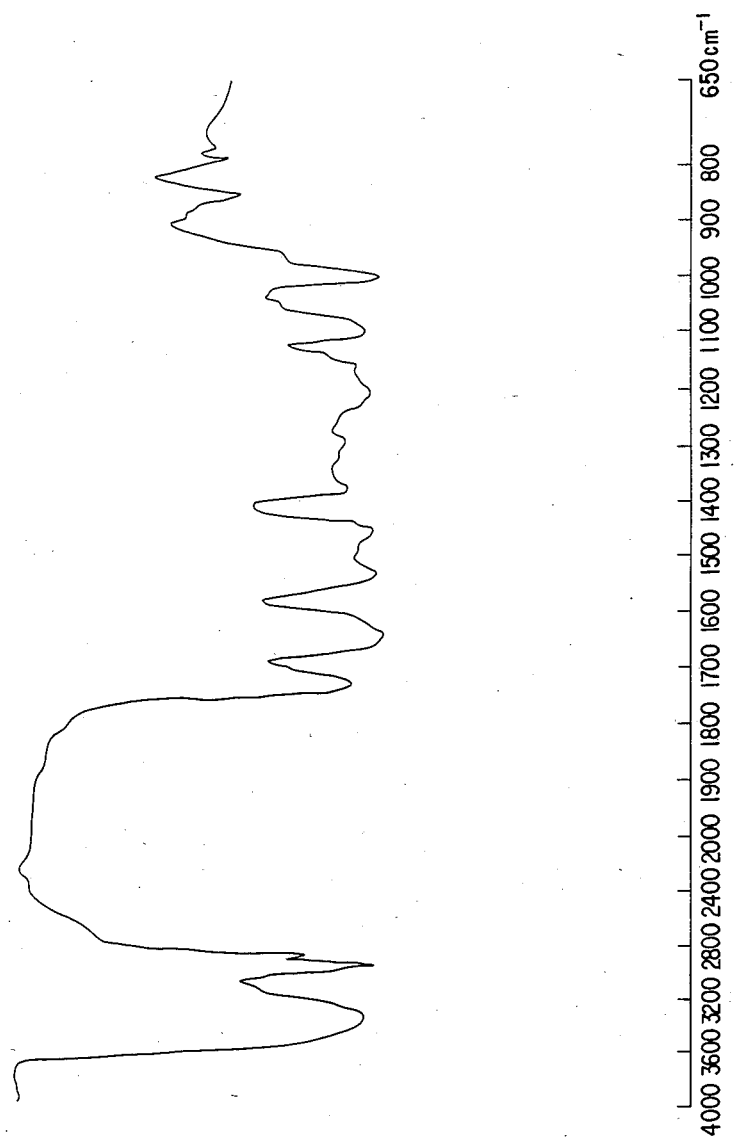
FIG. 3 is infrared absorption spectrum of T-23-IX.

3. Molecular weight: M$^+$626
4. Elementary analysis Calc. for C$_{35}$H$_{50}$N$_2$O$_3$: 67.09% C; 7.99% H; 4.47% N; 20.45% O. Found: 67.48% C; 8.11% H; 4.29% N; 20.12% O.
5. $[\alpha]_D^{25} = +211°$ C. (C=0.1, CH$_3$OH)
6. m.p. 139° C.
7. UV absorption spectrum (in CH$_3$OH)
λmax
261 nm (ε30,400)
271 nm (ε39,000)
281 nm (ε31,100)
305 nm (ε4,400)
8. IR absorption spectrum (in CHCl$_3$) (see FIG. 3)

| λ max | 3350 | 2950 | 1730 | 1640 |
|---|---|---|---|---|
| | 1530 | 1450 | 1380 | 1300 |
| | 1200 | 1100 | 1000 cm$^{-1}$ | |

9. Solubility:

Soluble in methanol, ethanol, acetone, ethyl acetate, chloroform and pyridine Insoluble in n-hexane, petroleum ether and water The T-23-VIII and -IX substances of the invention exhibit the physiological properties as shown below and they are expected for use in anti-tumor agents.

Anti-tumor activity (in vitro) against L-5178Y tumor cells

| T-23-VIII | | T-23-IX | |
|---|---|---|---|
| Conc. (μg/ml) | State of cell growth | Conc. (μg/ml) | State of cell growth |
| 2.0 | − | 2.0 | − |
| 1.0 | − | 1.0 | − |
| 0.5 | − | 0.5 | − |
| 0.25 | + | 0.25 | − |
| 0.125 | + | 0.125 | + |

The cell growth was observed by a dilution method using as Eagle-NEM medium (Nissui) supplemented with 10% horse serum and 100 mg/l asparagine and cultivated at 37° C. for 120 hours.

As stated hereinbefore, the elution of T-23-VIII substance was accompanied by the T-23-I substance, and the elution of the T-23-IX substance was accompanied by the T-23-II substance, and hence the T-23-VIII and T-23-IX substances may be purified separately. However, in comparison with the T-23-II and T-23-IX substances, the T-23-I and T-23-VIII substances were readily eluted from the silica gel column, and hence it was convenient to purify these substance according to the following procedure.

More particularly, the T-23-VIII is of the oxidation type and the T-23-IX substance is of the reduction type as mentioned previously, and they are interconvertible via a redox reaction. Therefore, the crude mixture obtained was dissolved in methanol containing ferric chloride ($FeCl_3$) and then stirred at room temperature to oxidize the T-23-II and T-23-IX substances contained therein to the T-23-I and T-23-VIII substances, respectively. Excess ethyl acetate was then added to the solution and repeatedly washed with water to remove the ferric chloride therefrom. The solution was then concentrated under reduced pressure to obtain an oily residue containing the T-23-I and T-23-VIII substances. The oily residue obtained was subjected to silica gel chromatography and eluted with chloroform/methanol (100:1). The eluate was fractionated into fractions of a definite amount, whereupon after the elution of the fraction containing the T-23-I, the fractions containing the T-23-I and -VIII came to be eluted. These fractions were collected and concentrated in vacuo to obtain yellow powder containing the T-23-I and -VIII substances. The yellow powder obtained was subjected to a preparative thin layer chromatography using silica gel and developed with benzene/ethyl acetate (1:1), and after drying and removing the solvent therefrom, the development was again effected with the same solvent, whereupon T-23-I appeared in the vicinity of $R_f=0.58$, and T-23-VIII in the vicinity of $R_f=0.56$. The fraction corresponding to the T-23-VIII was scraped out and eluted with chloroform/methanol (10:1). The eluate was concentrated in vacuo to obtain the T-23-VIII substance as yellow amorphous powder. The T-23-VIII substance thus obtained has the aforesaid physicochemical properties.

The T-23-IX substance was obtained by reducing the T-23-VIII substance with such reducing agent as sodium hydrosulfite ($Na_2S_2O_4$). The T-23-VIII substance was dissolved in ethyl acetate and stirred together with a 1% aqueous sodium hydrosulfite solution, and the ethyl acetate layer separated was repeatedly washed with water and then concentrated in vacuo to obtain an oily residue containing the T-23-IX substance. The oily residue was subjected to a preparative thin layer chromatography and developed with benzene/chloroform/methanol (3:7:3), and the fraction corresponding to the T-23-IX substance in the vicinity of $R_f=0.55$ was scraped out and eluted with chloroform/methanol (7:1). The eluate was concentrated in vacuo to obtain the T-23-IX substance as colorless amorphous powder. The T-23-IX substance thus obtained has the aforesaid physicochemical properties.

The following are the non-limitative examples to illustrate the present invention.

EXAMPLE 1

One loopful of strain T-23 incubated on a slant medium comprising 1.0% soluble starch, 0.2% yeast extract and 1.5% agar was inoculated into a Sakaguchi flask containing 100 ml of seed medium (comprising 1.0% soluble starch, 1.0% waste molasses, 1.0% meat extract and 1.0% polypeptone (pH 7.0)). The flask was incubated on a reciprocal shaker at 30° C. for 48 hours. A 0.5 ml aliquot of the culture was inoculated into a Sakaguchi flask containing 100 ml of the same medium and the culture was incubated on a reciprocal shaker at 30° C. for 24 hours thereby to obtain a seed inoculum for the production culture using a jar fermenter. For the production culture, six 30 l-capacity jar fermenters each containing 15.0 liters of a medium (pH 7.0) containing 1.0% glucose, 1.5% soluble starch, 1.5% soya flour, 0.2% dried yeast, 0.2% ammonium sulfate, 0.5% sodium chloride, 0.4% precipitated calcium carbonate and 0.33% antifoaming agent (Toshiba "Silicone" YMA 6509) were used. The inoculum obtained was added to each fermenter at the proportion of 4.0%, and cultivation with aeration and agitation (15.0 l/min., 200 r.p.m.) was carried out at 30° C. for 24 hours.

Immediately after completion of the cultivation, the mycelium was filtered off by means of a large type continuous centrifugal machine, soaked in 20 liters of 60% aqueous acetone solution with stirring for a short while and then allowed to stand for 3 hours. Then, the mycelium was filtered to obtain a supernatant. The same treatment was repeated twice. The extracts combined amounted up to 40 liters. From this, acetone was evaporated in vacuo thereby to leave 18.0 liters of an aqueous solution. To this solution (18.0 liters), 6.5 kg sodium chrolide was added, and the resulting solution was extracted twice with each 9.0 liters ethyl acetate. The ethyl acetate solution obtained was dried over $Na_2SO_4$ (1 Kg). The solution was concentrated to a small volume in vacuo. To the concentrated solvent, an adequate volume of hexane was added, thereby to precipitate the fractions containing T-23-I, -II, -VIII and -IX substances. The precipitate thus obtained was washed with hexane and then dried to obtain a crude mixture containing T-23-I, -II, -VIII and -IX substances. The crude mixture thus obtained was dissolved in 1 liter of methanol, and the solution was added with 20 g of ferric chloride and then stirred for 3 hours at room temperature. The solvent was evaporated in vacuo to obtain an oily residue containing the T-23-I and T-23-VIII substances. The oily residue thus obtained was dissolved in 2.5 liters of ethyl acetate, washed five times with saturated saline water, and the ethyl acetate layer was concentrated in vacuo to obtain an oily product.

The oily residue thus obtained was dissolved in 150 ml of chloroform, and the solution was chromatographed on a silica gel column (8 cm×40 cm) with chloroform/methanol (100:1). 2.5 Liters of the eluate first obtained was discarded as containing no active substance, and thereafter fractionated in each 15 ml portions. Each of the fractions collected were subjected to thin layer chromatography (developed twice with ethyl acetate/benzene=1:1) using a silica gel plate of Kieselgel 60$F_{254}$ (Art. 5715). The chromatograph obtained was examined under the light of 254 nm of UV lamp to confirm the presence of the T-23 substances, whereupon it was confirmed that the sixteenth to fiftieth fractions contained a pure T-23-I substance and the fifty-first to the sixty-fifth fractions contained both the T-23-I and T-23-VIII substances.

The fractions containing the T-23-I substance were concentrated in vacuo to remove the solvent therefrom, thereby obtaining 12.5 g of yellow powder of the T-23-I substance. The fractions containing both the T-23-I and T-23-VIII substances were also concentrated in vacuo to obtain likewise 0.6 g of yellow powder containing both the T-23-I and T-23-VIII substances. The powder thus obtained was dissolved in acetone, and the solution was subjected to silica gel thin layer chromatography (Merk's Kieselgel 60$F_{254}$ Art. 5744), developed with benzene/ethyl acetate (1:1) and dried, followed by development again with the same solvent. The chromatograph obtained was examined under the light of 254 nm of UV lamp. Thereby, it was confirmed that the T-23-I fraction appeared in the vicinity of $R_f=0.58$ and the T-23-VIII fraction appeared in the vicinity of $R_f=0.56$. This T-23-I fraction was scraped out and the resulting silica gel was packed in a column. A mixed solvent of chloroform/methanol (10:1) was passed through the column to elute the T-23-I substance, and the eluate obtained was concentrated in vacuo to obtain 0.5 g of yellow powder of the T-23-I substance. Similarly, the T-23-VIII fraction was scraped out and eluted in the same manner. The eluate obtained was concentrated in vacuo to obtain 50 mg of yellow powder of the T-23-VIII substance.

EXAMPLE 2

50 Mg of the T-23-VIII substance obtained in Example 1 were dissolved in 50 ml of ethyl acetate, and the solution was then stirred vigorously, together with 40 ml of a 0.5% aqueous sodium hydrosulfite solution, in a separating funnel until yellow color of the ethyl acetate layer disappeared. The resulting solution was allowed to stand still, and the aqueous layer was removed therefrom, and the remaining ethyl acetate layer was washed 5 times with saturated saline water, and was then concentrated in vacuo to obtain 50 mg of an oily residue. The oily residue thus obtained was dissolved in a small amount of acetone, and the solution was then subjected to silica gel thin layer chromatography (Merk's Kieselgel 60F254, Art. 5744), and developed with benzene/chloroform/methanol (3:7:3). Thereafter, the fraction in the vicinity of $R_f=0.55$ corresponding to the T-23-IX substance was confirmed by examining the chromatograph under the light of 254 nm of UV lamp, and the fraction was scraped out. The resulting silica gel was packed in a column, and chloroform/methanol (7:1) was passed through the column to elute the T-23-IX substance. The eluate obtained was concentrated in vacuo to obtain 3.5 mg of the T-23-IX substance in colorless amorphous powder.

What is claimed is:

1. A compound of the formula

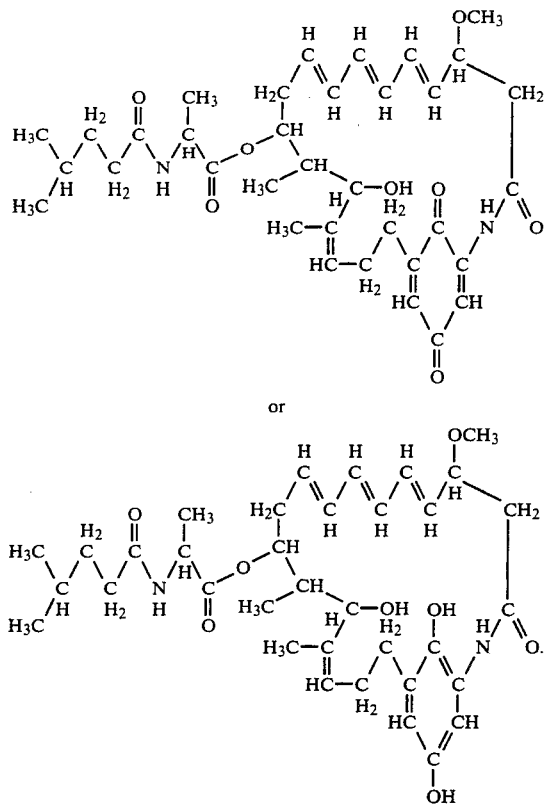

or

2. A method of treating tumors in a patient which comprises administering to said patient an antitumor effective amount of a compound of the formula

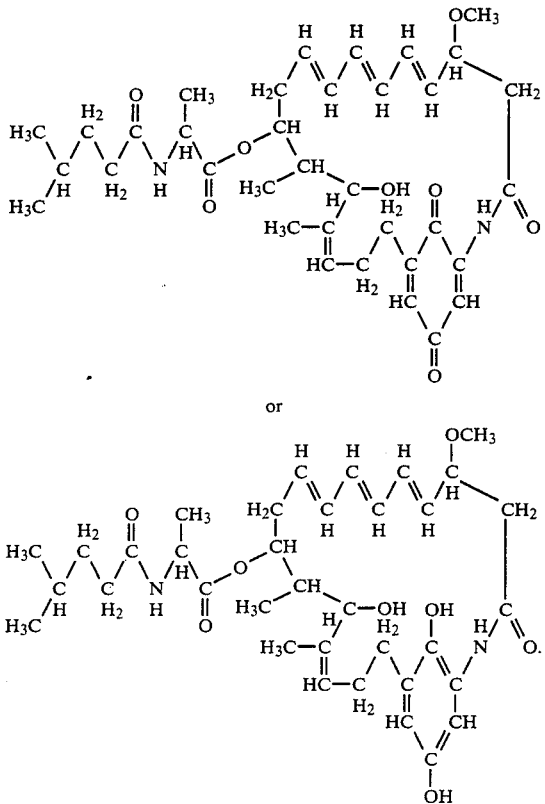

or

* * * * *

UNITED STATES PATENT AND TRADEMARK OFFICE
CERTIFICATE OF CORRECTION

PATENT NO. : 4,587,237
DATED : May 6, 1986
INVENTOR(S) : OTAKE, et al.

It is certified that error appears in the above-identified patent and that said Letters Patent is hereby corrected as shown below:

Amend formula in column 4 to read:

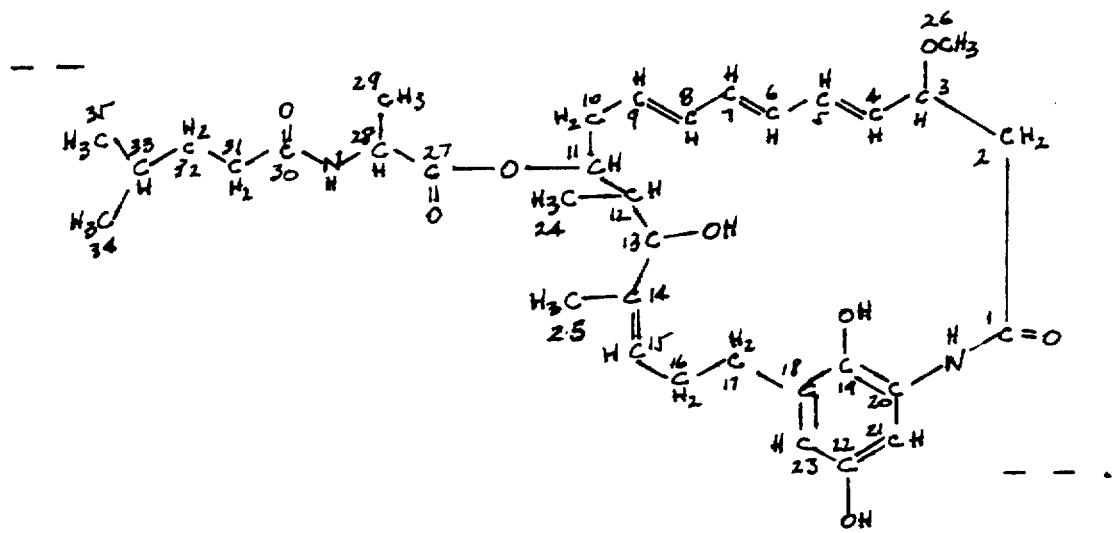

Signed and Sealed this

Twenty-eighth Day of October, 1986

[SEAL]

Attest:

DONALD J. QUIGG

Attesting Officer   Commissioner of Patents and Trademarks